United States Patent
Wu et al.

(10) Patent No.: US 8,160,206 B2
(45) Date of Patent: Apr. 17, 2012

(54) DUAL-ENERGY IMAGING AT REDUCED SAMPLE RATES

(75) Inventors: Xiaoye Wu, Rexford, NY (US); David Allen Langan, Clifton Park, NY (US); Jiang Hsieh, Brookfield, WI (US); Robert Franklin Senzig, Germantown, WI (US); Hao Lai, Rexford, NY (US); Dan Xu, Waukesha, WI (US); Thomas Matthew Benson, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 12/962,972

(22) Filed: Dec. 8, 2010

(65) Prior Publication Data
US 2011/0150183 A1    Jun. 23, 2011

Related U.S. Application Data

(60) Provisional application No. 61/289,822, filed on Dec. 23, 2009.

(51) Int. Cl.
*H05G 1/64* (2006.01)

(52) U.S. Cl. ............... 378/98.9; 378/4; 378/5; 382/130
(58) Field of Classification Search ............... 378/4, 5, 378/98.9, 98.12; 382/130
See application file for complete search history.

(56) References Cited

U.S. PATENT DOCUMENTS

| | | | | |
|---|---|---|---|---|
| 7,260,172 | B2 * | 8/2007 | Arenson et al. | 378/18 |
| 7,272,429 | B2 * | 9/2007 | Walker et al. | 600/407 |
| 7,298,812 | B2 * | 11/2007 | Tkaczyk et al. | 378/5 |
| 7,379,575 | B2 * | 5/2008 | Ruhrnschopf | 382/128 |
| 7,391,844 | B2 * | 6/2008 | Wu et al. | 378/18 |
| 7,801,265 | B2 * | 9/2010 | Yu et al. | 378/5 |

OTHER PUBLICATIONS

Maab et al., Exact dual energy material decomposition from inconsistent rays (MDIR), Med Phys, 38, Feb 2011, pp. 691-700.*

* cited by examiner

*Primary Examiner* — Alexander H Taningco
(74) *Attorney, Agent, or Firm* — Fletcher Yoder, PC

(57) ABSTRACT

The present disclosure relates to the generation of dual-energy X-ray data using a data sampling rate comparable to the rate utilized for single-energy imaging. In accordance with the present technique a reduced kVp switching rate is employed compared to conventional dual-energy imaging. Full angular resolution is achieved in the generated images.

20 Claims, 2 Drawing Sheets

DUAL-ENERGY IMAGING AT REDUCED SAMPLE RATES

CROSS-REFERENCE TO RELATED APPLICATIONS

This application is a Non-Provisional of U.S. Provisional Patent Application No. 61/289,822, entitled "Dual-Energy Imaging At Reduced Sample Rates", filed Dec. 23, 2009, which is herein incorporated by reference in its entirety for all purposes.

BACKGROUND OF THE INVENTION

The subject matter disclosed herein relates to non-invasive imaging and, in particular, to dual-energy imaging.

In the fields of medical imaging and security screening, non-invasive imaging techniques have gained importance due to benefits that include unobtrusiveness, convenience, and speed. In medical and research contexts, non-invasive imaging techniques are used to image organs or tissues beneath the surface of the skin. Similarly, in industrial or quality control (QC) contexts, non-invasive imaging techniques are used to examine parts or items for hidden defects that may not be evident from an external examination. In security screening, non-invasive imaging techniques are typically used to examine the contents of containers (e.g., packages, bags, or luggage) without opening the containers and/or to screen individuals entering or leaving a secure location.

A number of non-invasive imaging modalities exist today. One such technique, dual-energy (DE) radiography, involves the acquisition of X-ray attenuation data at different energies within a relatively small time interval. The attenuation data at the different energy levels may then be used to decompose the imaged anatomy and create a first image of a first material (e.g., water or bone) and a second image of a second material (e.g., iodine, or other contrast agents). Because of the need to acquire sufficient attenuation data at multiple X-ray energies, the data or imaging sampling rate may be significantly increased (e.g., doubled) relative to scans where data is acquired at only a single energy. Such increased sampling rates may be difficult to obtain because of the physical, electrical, and/or mechanical constraints imposed by the imaging system hardware. Further, the smaller view times associated with the faster sampling rate may result in increased noise relative to the useful signal in such sampling schemes. Accordingly, techniques are needed to overcome the problems associated with dual energy image acquisition and reconstruction. The techniques described herein are intended to address one or more of these problems associated with dual energy imaging systems.

BRIEF DESCRIPTION OF THE INVENTION

In one embodiment, a method for acquiring dual-energy projection data is provided. The method includes the act of alternately emitting X-rays corresponding to a low kVp and a high kVp such that a corresponding set of low kVp projection data is acquired for each low kVp emission and a corresponding set of high kVp projection data is acquired for each high kVp emission. The aggregate sets of low kVp projection data or high kVp projection data, when taken alone, do not provide full angular resolution. But the combined sets of low kVp projection data and high kVp projection data provide full angular resolution. A mixed kVp image is generated using the combined low kVp projection data and high kVp projection data. A seed image is generated based upon the mixed kVp image. The seed image is updated to generate an updated image. The updated image is reprojected to generate density projections at full angular resolution. One or more of high kVp images, low kVp images, material decomposition images, or monochromatic images are generated based at least in part on the generated density projections.

In another embodiment, a method for acquiring dual-energy projection data is provided. The method includes the act of alternately generating X-rays corresponding to a low kVp and a high kVp such that a corresponding set of low kVp projection data is acquired for each low kVp emission and a corresponding set of high kVp projection data is acquired for each high kVp emission. A mixed kVp image is generated using the combined low kVp projection data and high kVp projection data. A seed image approximating one basis material is generated based upon the mixed kVp image. The seed image is updated to generate an updated image. The updated image is reprojected to generate density projections at full angular resolution. The generated density projections are used to compute missing angular views for the set of low kVp projection data or the set of high kVp projection data. One or more of high kVp images, low kVp images, material decomposition images, or monochromatic images are generated based at least in part on the one or more computed missing angular views for the set of low kVp projection data or the set of high kVp projection data.

In a further embodiment, a multi-energy imaging system is provided. In one such embodiment, the multi-energy imaging system includes an X-ray source capable of emitting X-rays at a low kVp and a high kVp and a detector assembly capable of generating signals in response to the emitted X-rays. The imaging system also includes a data acquisition system configured to acquire the signals generated by the detector assembly such that a corresponding set of low kVp projection data is acquired for each low kVp emission and a corresponding set of high kVp projection data is acquired for each high kVp emission, wherein the aggregate sets of low kVp projection data or high kVp projection data, when taken alone, do not provide full angular resolution but the combined sets of low kVp projection data and high kVp projection data provide full angular resolution. In addition, the imaging system includes image processing circuitry configured to execute one or more algorithms. When executed by the image processing circuitry, the one or more algorithms: generate a mixed kVp image using the combined low kVp projection data and high kVp projection data; extract a seed image based upon the mixed kVp image; update the seed image to generate an updated image; reproject the updated image to generate density projections at full angular resolution; and generate one or more of high kVp images, low kVp images, material decomposition images, or monochromatic images based at least in part on the generated density projections.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

As described in detail below, embodiments of a dual-energy (DE) imaging system and techniques are provided for producing materially decomposed (MD) and/or monochromatic images with little or no increase in the sampling rate as compared to the acquisition of image data at a single-energy. This approach utilizes a basis material decomposition algorithm that allows the kVp (kilivolts peak) switching rate (associated with switching between the two X-ray energies used for dual-energy data acquisition) to be reduced by half compared to conventional dual-energy approaches. In one embodiment of the present approach, a mixed kVp image is obtained at full angular resolution. A seed image corresponding to one basis material is extracted and updated. The updated basis material image is then used to generate full angular resolution low- or high-energy images, basis material images, or monochromatic images. Although the embodiments illustrated herein are described in a medical imaging context, it should be noted that the presently contemplated techniques may also be applicable in security or quality control contexts.

Figure 1:
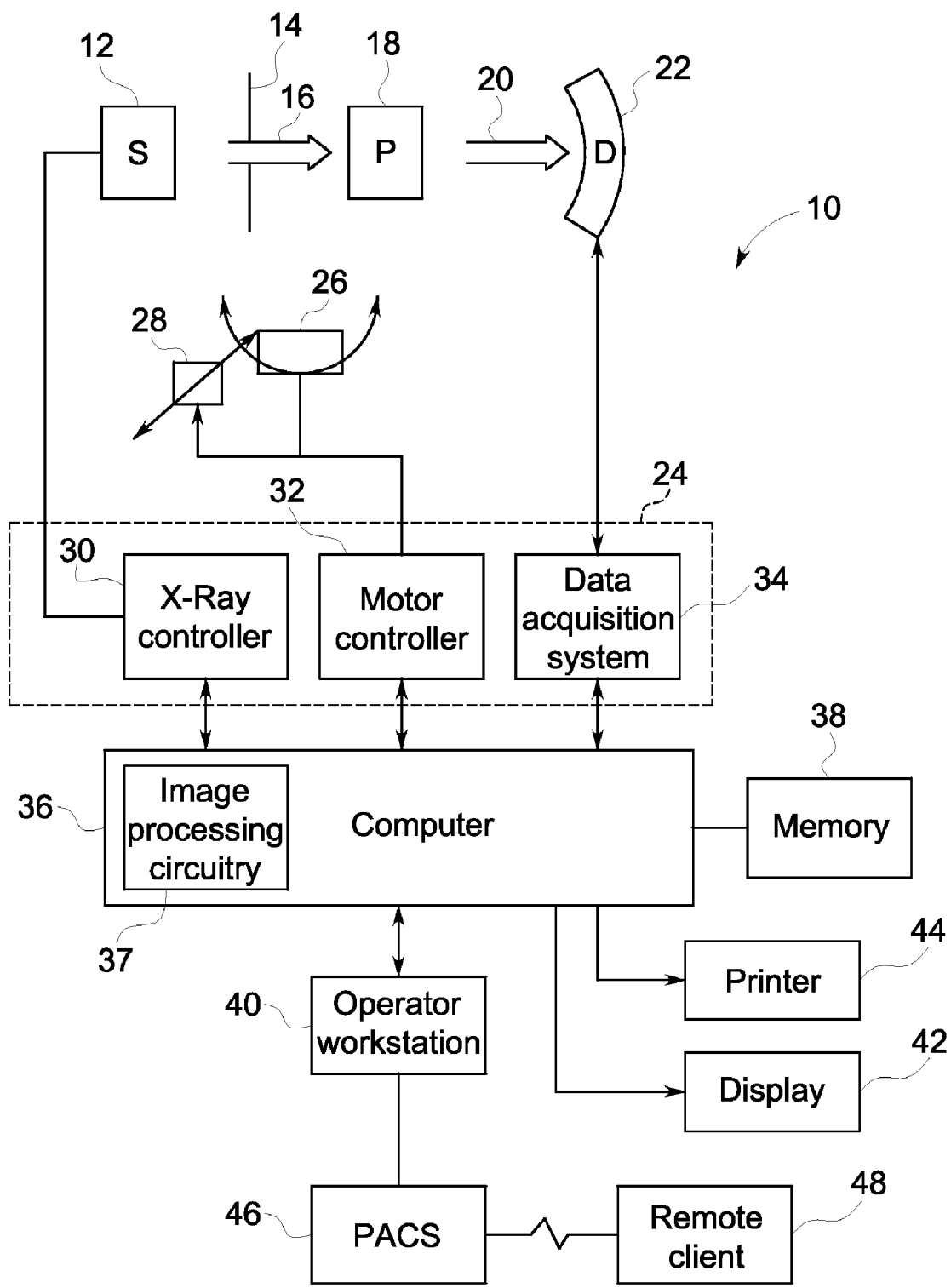
FIG. 1 is a perspective view of a dual-energy (DE) X-ray imaging system in accordance with an embodiment of the present technique.

With the foregoing in mind and turning now to the drawings, FIG. 1 illustrates a multi-energy X-ray imaging system 10 that may be used in accordance with the present techniques. In the illustrated embodiment, the multi-energy X-ray imaging system 10 is a digital X-ray system that is designed to both acquire and process image data for display. The system 10 is capable of acquiring X-ray attenuation image data at two or more X-ray energy levels. For example, in one embodiment, the system 10 is capable of acquiring projection data of a region of interest using X-rays at a first energy level (e.g., high energy) as well as using X-rays at a second, different energy level (e.g., low energy). Further, the depicted system 10 may acquire projection data at a variety of angular positions. For the different angular positions, image data may be acquired at both X-ray energy levels or at only one of the X-ray energy levels. The multi-energy X-ray imaging system 10 (e.g., a dual-energy imaging system) may be used to produce images based on the data acquired at the different X-ray energy levels (i.e., high energy and low energy images), based on different basis materials (e.g., bone images, water images, contrast images, and so forth), or based on a specified wavelength (i.e., a monochromatic image).

For example, with respect to basis material images, a first basis material and a second basis material will have different absorption characteristics for the low energy X-rays and the high energy X-rays generated by the system 10, enabling the system 10 to distinguish the absorption of X-rays caused by the first basis material and the absorption caused by the second basis material. Such differential absorption allows the system 10 to be operable to produce both high energy projections and low energy projections that may be materially decomposed (based on these differential absorption characteristics) to produce basis material images (e.g., water images, bone images, iodine images, calcium images, etc.) for further analysis of the desired anatomy. Though the illustrated imaging system 10 is discussed in the context of medical imaging, the techniques and configurations discussed herein are applicable in other non-invasive imaging contexts, such as security screening or industrial nondestructive evaluation of manufactured parts.

In the embodiment illustrated in FIG. 1, the multi-energy imaging system 10 is depicted as a computed tomography (CT) imaging system that includes an X-ray source 12. The X-ray source is configured to generate X-ray at different energy levels, as discussed herein. The source 12 may be positioned proximate to a collimator 14. The collimator 14 may consist of one or more collimating regions, such as lead or tungsten shutters, for each emission point of the source 12. The collimator 14 typically defines the size and shape of the one or more X-ray beams 16 that pass into a region in which a subject 18, such as a human patient, is positioned. Each X-ray beam 16 may be generally fan-shaped or cone-shaped, depending on the configuration of the detector array and/or the desired method of data acquisition, as discussed below. An attenuated portion 20 of each X-ray beam 16 passes through the subject 18 and impacts a detector array, represented generally at reference numeral 22.

The illustrated system 10 may include one or more collimators 14 or filters that shape or limit an emitted stream of radiation directed toward a region in which the subject 18 is positioned. However, in some embodiments, the system 10 may not include a collimator, and images may be obtained using the full field of view of the system 10. Alternatively, in certain embodiments, the field of view of the system 10 may be reduced by using the collimator 14 to reduce the spread of X-rays produced by the X-ray source 12. The collimator 14 can be selectively placed over the X-ray source 12 when desired or the collimator 14 may be kept disposed over the X-ray source 12. Additionally, the collimator 14 may be adjustable so that full (or wide) field of view and reduced (or narrow) field of view images may be obtained with the collimator disposed over the X-ray source 12. It should be noted that the present techniques may be used in an imaging system having a standard collimator, a slit collimator, any other suitable collimator, or no collimator at all.

The detector 22 is generally formed by a plurality of detector elements that detect the X-ray beams 16 after they pass through or around the subject 18. Each detector element produces an electrical signal that represents the intensity of the X-ray beam 16 incident at the position of the detector element when the beam strikes the detector 22. Alternatively, each element of detector 22 may count incident photons in the X-ray beam 16 and may also determine their energy. Typically, the X-ray beam 16 is generated and the corresponding electrical signals are acquired at a variety of angular positions around the subject of interest so that a plurality of radiographic projection views can be collected. The electrical signals are acquired and processed to reconstruct an image that is indicative of the features within the subject 18, as discussed in further detail below.

It should be noted that the digital X-ray detector 22 may be any detector that is operable to perform dual-energy X-ray imaging. For instance, the digital X-ray detector 22 may be an amorphous silicon flat panel that has the ability to acquire two images in rapid succession. Additionally, the detector 22 may include energy discriminative detector materials that are capable of separating X-ray photons from one acquisition into two energy bins. Such detectors may be useful in acquiring data via energy discrimination or photon counting approaches. That is, the digital detector 22 may be capable of facilitating image acquisition speeds that enable the acquisition of high and low energy images with large energy separation (mean energy separations in spectra as high as approximately 90 keV), which may translate to improved image subtraction. In one embodiment, the X-ray detector 22 converts the X-ray photons received on its surface to lower energy photons, and subsequently to electric signals, which are acquired and processed to reconstruct one or more images of the features within the subject.

A system controller 24 commands operation of the imaging system 10 to execute examination protocols and to process the acquired data. The source 12 is typically controlled by the system controller 24. Generally, the system controller 24 furnishes power, focal spot location, control signals and so forth, for the multi-energy examination sequences. The detector 22 is coupled to the system controller 24, which commands acquisition of the signals generated by the detector 22. The system controller 24 may also execute various signal processing and filtration functions, such as initial adjustment of dynamic ranges, interleaving of digital image data, and so forth. In the present context, system controller 24 may also include signal-processing circuitry and associated memory circuitry. As discussed in greater detail below, the associated memory circuitry may store programs and/or routines executed by the system controller 24 or a processor-based system in communication with the system controller 24, such as programs or routines for implementing the presently disclosed techniques. Further, the memory circuitry of the system controller 24 may also store configuration parameters, image data, and so forth. In one embodiment, the system controller 24 may be implemented as all or part of a processor-based system such as a general purpose or application-specific computer system.

In the illustrated embodiment of FIG. 1, the system controller 24 may control the movement of a linear positioning subsystem 28 and a rotational subsystem 26 via a motor controller 32. In an embodiment where the imaging system 10 includes rotation of the source 12 and/or the detector 22, the rotational subsystem 26 may rotate the source 12, the collimator 14, and/or the detector 22 about the subject 18. It should be noted that the rotational subsystem 26 might include a gantry comprising both stationary components (stator) and rotating components (rotor). The linear positioning subsystem 28 may enable the subject 18, or more specifically a patient table that supports the subject 18, to be displaced linearly. Thus, the patient table may be linearly moved within the gantry or within an imaging volume (e.g., the volume located between the source 12 and the detector 22) and enable the acquisition of data from particular areas of the subject 18 and, thus the generation of images associated with those particular areas. Additionally, the linear positioning subsystem 28 may displace the one or more components of the collimator 14, so as to adjust the shape and/or direction of the X-ray beam 16. In embodiments comprising a stationary source 12 and a stationary detector 22, a mechanical rotational subsystem may be absent, with emitters spaced at different angular locations about the subject instead being activated at different times to allow acquisition of projections at different angles. Similarly, in embodiments in which the source 12 and the detector 22 are configured to provide extended or sufficient coverage along the z-axis (i.e., the axis associated with the main length of the subject 18) and/or linear motion of the subject is not required, the linear positioning subsystem 28 may be absent.

The source 12 may be controlled by an X-ray controller 30 disposed within the system controller 24. The X-ray controller 30 may be configured to provide power and timing signals to the source 12. In addition, the X-ray controller may operate to control the energy level of the X-rays emitted by the source 12 at any given time. In addition, in some embodiments the X-ray controller 30 may be configured to selectively activate the source 12 such that tubes or emitters at different locations within the system 10 may be operated in synchrony with one another or independent of one another.

Further, the system controller 24 may comprise a data acquisition system 34. In such an embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor-based system, such as a computer 36. Alternatively, in other embodiments, the detector 22 may convert the sampled analog signals to digital signals prior to transmission to the data acquisition system 34.

In the depicted embodiment, a computer 36 is coupled to the system controller 24. The data collected by the data acquisition system 34 may be transmitted to the computer 36 for subsequent processing and reconstruction. For example, the data collected from the detector 22 may undergo pre-processing and calibration at the data acquisition system 34 and/or the computer 36 to produce representations of the line integrals of the attenuation coefficients of the subject 18 and the scanned objects. In one embodiment, the computer 36 contains image-processing circuitry 37 for processing and filtering the data collected from the detector 22. The processed data, commonly called projections, may then be reconstructed by the image processing circuitry 37 to form an image of the subject 18 and/or the scanned area. In one implementation, the projections are reconstructed into high- and/or low energy images, materially decomposed (MD) images, and/or monochromatic images, in accordance with the techniques discussed herein. For example, the image processing circuitry 37 may include instructions for receiving acquired image data, generating high- or low-energy images, materially decomposed images, or monochromatic images in accordance with the techniques described in detail below, and outputting the generated images via an output device, such as the display 42, a printer 44, or the like. Once reconstructed, the images produced by the system 10 of FIG. 1 may reveal an internal region of interest of the subject 18 which can be used for diagnosis, evaluation, and so forth.

The computer 36 may comprise or communicate with a memory 38 that can store data processed by the computer 36, data to be processed by the computer 36, or routines and/or algorithms to be executed by the computer 36, such as for processing image data in accordance with the present techniques. It should be understood that any type of computer accessible memory device capable of storing the desired amount of data and/or code may be utilized by such a system 10. Moreover, the memory 38 may comprise one or more memory devices, such as magnetic, solid-state, or optical devices, of similar or different types, which may be local and/or remote to the system 10. The memory 38 may store data, processing parameters, and/or computer programs comprising one or more routines or algorithms for performing the image processing and reconstruction techniques described herein.

The computer 36 may also be adapted to control features enabled by the system controller 24 (i.e., scanning operations and data acquisition). Furthermore, the computer 36 may be configured to receive commands and scanning parameters from an operator via an operator workstation 40 which may be equipped with a keyboard and/or other input devices. An operator may, thereby, control the system 10 via the operator workstation 40. Thus, the operator may observe from the computer 36 the reconstructed image and other data relevant to the system 10, initiate imaging, select and apply image filters, and so forth. Further, the operator may manually identify and/or review features and regions of interest from the reconstructed image. Automated detection algorithms may be applied to aid in identifying and/or manipulating the features or regions of interest.

As illustrated, the system 10 may also include a display 42 coupled to the operator workstation 40. The display 42 may be utilized to observe the reconstructed images, for instance. Additionally, the system 10 may include a printer 44 coupled to the operator workstation 40 and configured to print a copy of the one or more reconstructed images. The display 42 and the printer 44 may also be connected to the computer 36 directly or via the operator workstation 40. Further, the operator workstation 40 may include or be coupled to a picture archiving and communications system (PACS) 46. It should be noted that PACS 46 might be coupled to a remote system 48, radiology department information system (RIS), hospital information system (HIS) or to an internal or external network, so that others at different locations can gain access to the image data.

Although only one operator workstation is depicted, one or more operator workstations 40 may be linked in the system 10 for outputting system parameters, requesting examinations, viewing images, and so forth. In general, displays 42, printers 44, workstations 40, and similar devices supplied within the system 10 may be local to the data acquisition components, or may be remote from these components, such as elsewhere within an institution or hospital, or in an entirely different location, linked to the image acquisition system 10 via one or more configurable networks, such as the Internet, virtual private networks, and so forth. Furthermore, although the previous discussion discloses typical embodiments of the imaging system 10, any other suitable system configuration may be employed to acquire image data and process such data via the techniques described herein.

With the foregoing system discussion in mind, an imaging system 10 as described above may be used in multi, e.g., dual, energy imaging protocols. In conventional approaches, the kVp associated with the X-ray source might be modulated rapidly between a low and high kVp setting to achieve the desired X-ray energy profile for a data acquisition. In such a conventional, approach, the number of views at low or high kVp has to be sufficient enough individually such that each of the kVp projections can form an image without view starvation artifacts. As a result, during a scan, the sampling rate has to be doubled compared to that of a single kVp scan. Such an increased sampling scheme reduces the effective photon energy separation between the low and high kVp due to the finite high voltage ramp up and ramp down slope. In addition, the signal to electronic noise ratio is increased as a result of the reduced view time. In accordance with the present disclosure, a basis material decomposition approach is described in which the sampling rate is not doubled while sufficient angular resolution is maintained.

In conventional basis material decomposition (BMD), measurements of low and high kVp projection rays fully aligned in space are acquired. These high- and low kVp projections are transformed to a new set of projections, each representing the density line integration of corresponding basis material along the ray path, as mathematically described in the following:

$$m_1 = F_1(p_{low}, p_{high}) \quad (1)$$

$$m_2 = F_2(p_{low}, p_{high}) \quad (2)$$

where, $m_1$ and $m_2$ are the density integral of materials 1 and 2, respectively, $p_{low}$ and $p_{high}$ are the measured and processed projections at low and high kVp, and F( ) functions are derived from system calibration.

In this conventional approach, for decomposition to be performed, $p_{low}$ and $p_{high}$ are projections at the same ray path. In a fast kVp switching implementation, $p_{low}$ in the $p_{high}$ ray path is obtained by interpolating among low kVp projections in the vicinity around $p_{high}$ ray path to the precise $p_{high}$ ray path, or vice versa. To avoid the loss of angular resolution, high view numbers of low and high kVp projections are employed, resulting in the use of a fast switching mode. The rapid switching decreases the time duration of low and high kVp states, relatively increasing the portion of the kVp transition time in both low and high views. As a result, the effective energy separation between the two projections narrows. In addition, the signal to electronic noise ratio decreases. The energy narrowing effect leads to elevated noise in the decomposed projections $m_1$ and $m_2$ due to the nature of the BMD process. In general, the more energy separation between low and high kVp states, the better noise characteristic in the decomposed material density images.

Figure 2:
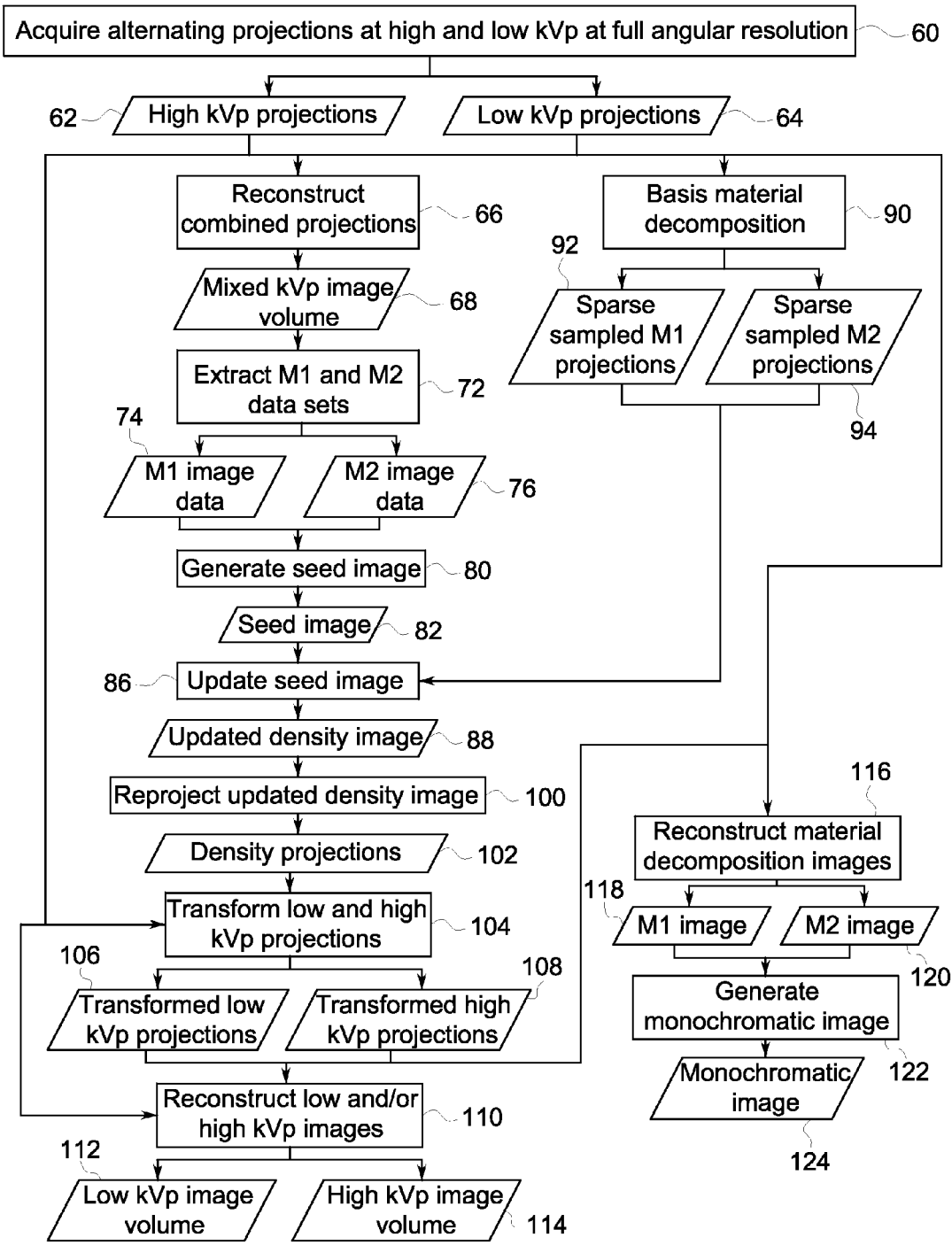
FIG. 2 is a flowchart depicting steps of a dual-energy imaging algorithm in accordance with an embodiment of the present technique.

In accordance with the present approach, the same angular resolution for the basis material decomposed images is maintained despite a relatively slow kVp switching rate being employed in the scan. For example, referring now to FIG. 2, in one implementation low and high kVp X-ray emissions are alternated sequentially (block 60), with the total number of angular views of low and high kVp projections 62, 64 sufficient to satisfy the required angular resolution. In accordance with one such implementation, the sampling rate is approximately half that of a direct basis material decomposition. In the depicted embodiment, the low and high kVp projections 62, 64 are not separated to form individual images, but are instead combined (block 66) together to form a mixed kVp image volume 68. The mixed kVp image volume 68, $Img_{mix}$ (x, y, z), is equivalent to a middle or intermediate kVp image. That is, in one implementation the mixed kVp image volume 68 approximates an image volume obtained at 120 kVp when the low-energy and high-energy X-ray emissions are obtained at 80 kVp and 140 kVp respectively. No additional artifacts are typically observed in the mixed kVp image volume 68 compared to images reconstructed using the respective low or high kVp with full angular views, i.e., conventional high-energy images and low-energy images.

Image data related to material decomposition pairs of interest 74, 76 may be approximately extracted (block 72) from the mixed kVp image volume 68 and/or image data not related to such basis materials of interest may be excluded or removed from the mixed kVp image volume 68. For example, in one implementation bone and iodine data points are individually extracted from the mixed kVp image volume 68 and non-contrast enhanced soft tissue is eliminated. Such an example may pertain to an implementation in which iodine (i.e., contrast) and bone (e.g., calcium) material decomposition images are to be generated. In one implementation, intensity value thresholds (such as based upon threshold values of Hounsfield units (HU)) may be employed to perform the extraction. In another implementation, bone may be segmented from iodine, such as by employing a bone location-contour and HU differences.

The extracted image data 74, 76 may be used to generate (block 80) a seed image 82 for use in subsequent processing. As may be appreciated, the seed image 82 has the full angular resolution since it is extracted from the mixed kVp image volume 68 which posses full angular resolution. For example, in the above implementation the segmented bone HU image data points and contrast solution HU image data points are separately transformed to pure iodine density representations based on a pre-knowledge of high and low kVp spectra, the bone composition and the difference between pure iodine and the iodine solution set. In this example, the new image volume serves as a seeding non-water object image, e.g. seed image 82. The more accurate the seed image 82 when generated, the less intensity modification is needed in the later stages. In the present example, in the seed image 82, small vessels and lesions with insufficient iodine contrast may be missed and there may be a difference between the transformed iodine density image and the true iodine density.

Such a difference may be reduced or eliminated by updating (block 86) the seed iodine image using sparsely sampled projections from direct projection based basis material decomposition to generate an updated or true density image 88. For instance, in keeping with the previous example, to update the seed iodine image, sparsely sampled (half the view number, or less) projections $m_1$ and $m_2$ (92, 94) from a direct basis material decomposition (block 90) are obtained from angularly aligned low and high kVp projections $p_{low}$ and $p_{high}$ by interpolation in the angular direction. In such an example, where $m_2$ is the iodine projection, the difference projection $p_{update}$ of $m_2$ and reprojected rays from the seed iodine $p_i$ at the same angular direction is computed.

$$p_{update} = R(m_2) - p_i \quad (3)$$

where operator R( ) matches the spatial resolution of the iodine projections from direct basis material decomposition to that from the reprojected rays $p_i$ based on the seed image 82.

A difference image can be reconstructed from difference projection $p_{update}$ of $m_2$ and added to the seed iodine image to form the updated iodine image 88. If the seed iodine image is very close to the true iodine image, the difference image is small in magnitude, adding limited noise contamination to the seed image 82. The difference image may contain image data representing the small vessels and/or other small features that are missing in the seed image 82, and it may also correct for inaccurate density values of the iodine in the seed image 82 to the true iodine density representation. Both of these features in the updating process help provide an accurate iodine density image, on which generation of subsequent images discussed herein rely. The update is physically accurate due to the fact that in material decomposition space, the beam hardening effect is greatly minimized.

The updated density or material image 88 is reprojected (block 100) to obtain iodine density projections 102 at full angular resolution. For example, let $p_{id}$ be the reprojected iodine density projection 102 in the angular direction corresponding to the initially sampled low and high kVp projections 62, 64. The low kVp and high kVp projections 62, 64 can be inter-transformed (block 104) with the help of $p_{id}$. The transformation may take the following functional forms in one embodiment, which can be captured during system calibration.

$$p_{low\_transformed} = T_{low2high}(p_{high}, p_{id}) \quad (4)$$

$$p_{high\_transformed} = T_{high2low}(p_{low}, p_{id}) \quad (5)$$

After the transformation, the missing angular views in the initial low or high kVp projections are patched and full angular resolution kVp images 112, 114 may be generated (block 110) using the transformed and original kVp projection sets. In addition, upon generation of the full angular resolution low and high kVp projections, the corresponding material decomposition images 118, 120, such as a water and iodine image pair, can be effectively computed (block 116). Further, monochromatic images 124 may be generated (block 122) using the transformed and original sets of kVp projections. This process may be performed after obtaining the material decomposition images 118, 120, by proper weighting of the two material decomposition images 118, 120, as the following, $$Im_{mono} = Im_{m1}\mu_{m1}(E) + Im_{m2}\mu_{m2}(E) \quad (6)$$

where, $Im_{m1}$ and $Im_{m2}$ are the two material decomposition images 118, 120 (in the example above the water and iodine images respectively) with corresponding mass attenuation coefficients $\mu_{m1}(E)$ and $\mu_{m2}(E)$ at energy E.

Thus, by using the basis material decomposition algorithm disclosed herein, fast kVp switching rate can be effectively reduced by a factor of 2. This reduction in switching frequency can significantly increase the energy separation between the low and high kVp projections, thus providing reduced noise in the materially decomposed images. Further, the typical images associated with dual energy scanning can be deduced without loss of angular resolution and without view starvation artifacts. This algorithm may be useful in dual energy cardiac imaging where fast sampling rates are needed due to the temporal resolution requirements imposed by the beating heart. Thus, the present algorithm offers an alternative to effectively reduce the sample-rate typically associated with dual energy scanning. Further, in accordance with this algorithm, the sampling does not have to follow a one-low and one-high kVp pattern. For example, the low kVp samples can be further reduced as long as they do not create view starvation artifact in the iodine density image updating process.

Technical effects of the invention include generation of high and/or low kVp images, materially decomposed images, and/or monochromatic images at a reduced kVp switching rate. Other technical effects include generating materially decomposed (or other) images associated with dual-energy scanning that have the same angular resolution as when generated by conventional techniques but at a kVp switching rate that is essentially half the switching rate used in the conventional techniques. Further, a technical effect of the present disclosure is a multi- or dual-energy imaging system that executes multi- or dual-energy imaging protocols in which the sampling rate is not doubled but where angular resolution is maintained.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for acquiring dual-energy projection data, comprising:
   alternately emitting X-rays corresponding to a low kVp and a high kVp such that a corresponding set of low kVp projection data is acquired for each low kVp emission and a corresponding set of high kVp projection data is acquired for each high kVp emission, wherein the aggregate sets of low kVp projection data or high kVp projection data, when taken alone, do not provide full angular resolution but the combined sets of low kVp projection data and high kVp projection data provide full angular resolution;
   generating a mixed kVp image using the combined low kVp projection data and high kVp projection data;
   extracting a seed image based upon the mixed kVp image;
   updating the seed image to generate an updated image;
   reprojecting the updated image to generate density projections at full angular resolution;

generating one or more of high kVp images, low kVp images, material decomposition images, or monochromatic images based at least in part on the generated density projections.

2. The method of claim 1, wherein extracting the seed image comprises extracting one or more of bone image data, iodine image data, or water image data.

3. The method of claim 1, wherein updating the seed image comprises using sparsely sampled projections generated from a basis material decomposition process.

4. The method of claim 1, wherein updating the seed image comprises generating a difference image and adding the difference image to the seed image to generate the updated image.

5. The method of claim 1, wherein generating one or more of high kVp images, low kVp images, material decomposition images, or monochromatic images based at least in part on the generated density projections comprises computing one or more missing angular views for the set of low kVp projection data or the set of high kVp projection data.

6. The method of claim 1, wherein the sampling rate associated with acquisition of low kVP projection data and high kVp projection data is approximately half that of a direct basis material decomposition.

7. A method for acquiring dual-energy projection data, comprising:
    alternately generating X-rays corresponding to a low kVp and a high kVp such that a corresponding set of low kVp projection data is acquired for each low kVp emission and a corresponding set of high kVp projection data is acquired for each high kVp emission;
    generating a mixed kVp image using the combined low kVp projection data and high kVp projection data;
    extracting a seed image approximating one basis material based upon the mixed kVp image;
    updating the seed image to generate an updated image;
    reprojecting the updated image to generate density projections at full angular resolution;
    using the generated density projections to compute missing angular views for the set of low kVp projection data or the set of high kVp projection data; and
    generating one or more of high kVp images, low kVp images, material decomposition images, or monochromatic images based at least in part on the one or more computed missing angular views for the set of low kVp projection data or the set of high kVp projection data.

8. The method of claim 7, wherein the one or both of the set of low kVp projection data and the set of high kVp projection data provide less than a full angular range.

9. The method of claim 7, wherein a sampling rate used to generate the set of low kVp projection data and the set of high kVp projection data is generally equal to a sampling rate used to generate projection data at a single kVp.

10. The method of claim 7, wherein the mixed kVp image is equivalent to an image that would be generated at a kVp intermediate to the low kVp and the high kVp.

11. The method of claim 7, wherein extracting the seed image comprises employing a Hounsfield unit (HU) threshold or a segmentation approach.

12. The method of claim 7, wherein the seed image has full angular resolution.

13. The method of claim 7, wherein updating the seed image comprises updating the seed image with sparsely sampled projections from a direct projection based basis material decomposition.

14. The method of claim 7, wherein the sampling rate associated with acquisition of low kVP projection data and high kVp projection data is approximately half that of a direct basis material decomposition.

15. A multi-energy imaging system, comprising:
    an X-ray source capable of emitting X-rays at a low kVp and a high kVp;
    a detector assembly capable of generating signals in response to the emitted X-rays;
    a data acquisition system configured to acquire the signals generated by the detector assembly such that a corresponding set of low kVp projection data is acquired for each low kVp emission and a corresponding set of high kVp projection data is acquired for each high kVp emission, wherein the aggregate sets of low kVp projection data or high kVp projection data, when taken alone, do not provide full angular resolution but the combined sets of low kVp projection data and high kVp projection data provide full angular resolution; and
    image processing circuitry configured to execute one or more algorithms which, when executed by the image processing circuitry:
        generate a mixed kVp image using the combined low kVp projection data and high kVp projection data;
        extract a seed image based upon the mixed kVp image;
        update the seed image to generate an updated image;
        reproject the updated image to generate density projections at full angular resolution;
        generate one or more of high kVp images, low kVp images, material decomposition images, or monochromatic images based at least in part on the generated density projections.

16. The multi-energy imaging system of claim 15, wherein the seed image is updated using sparsely sampled projections generated from a basis material decomposition process.

17. The multi-energy imaging system of claim 15, wherein the seed image is updated by generating a difference image and adding the difference image to the seed image to generate the updated image.

18. The multi-energy imaging system of claim 15, wherein the one or more high kVp images, low kVp images, material decomposition images, or monochromatic images are generated by computing one or more missing angular views for the set of low kVp projection data or the set of high kVp projection data.

19. The multi-energy imaging system of claim 15, wherein the sampling rate associated with acquisition of low kVP projection data and high kVp projection data is approximately half that of a direct basis material decomposition.

20. The multi-energy imaging system of claim 15, wherein the mixed kVp image is equivalent to an image that would be generated at a kVp intermediate to the low kVp and the high kVp.

* * * * *